US006926735B2

(12) United States Patent
Henderson

(10) Patent No.: US 6,926,735 B2
(45) Date of Patent: Aug. 9, 2005

(54) MULTI-LUMEN VASCULAR GRAFTS HAVING IMPROVED SELF-SEALING PROPERTIES

(75) Inventor: Jamie S. Henderson, Oakland, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 133 days.

(21) Appl. No.: 10/328,081

(22) Filed: Dec. 23, 2002

(65) Prior Publication Data

US 2004/0122507 A1 Jun. 24, 2004

(51) Int. Cl.⁷ .................................................. A61F 2/06
(52) U.S. Cl. ..................... 623/1.42; 623/1.43; 623/1.27
(58) Field of Search .............................. 623/1.44, 1.42, 623/1.43, 1.13, 1.27, 1.39

(56) References Cited

U.S. PATENT DOCUMENTS

| | | | |
|---|---|---|---|
| 4,416,028 A | * | 11/1983 | Eriksson et al. ............ 623/1.38 |
| 4,619,641 A | | 10/1986 | Schanzer |
| 4,743,480 A | | 5/1988 | Campbell et al. |
| 4,816,339 A | | 3/1989 | Tu et al. |
| 4,969,896 A | | 11/1990 | Shors |
| 5,024,671 A | * | 6/1991 | Tu et al. ..................... 623/1.54 |
| 5,192,310 A | | 3/1993 | Herweck et al. |
| 5,931,865 A | | 8/1999 | Silverman et al. |
| 6,053,939 A | | 4/2000 | Okuda et al. |
| 6,319,279 B1 | | 11/2001 | Shannon et al. |
| 6,428,571 B1 | | 8/2002 | Lentz et al. |
| 2002/0091440 A1 | * | 7/2002 | Calcote ...................... 623/1.42 |
| 2003/0153983 A1 | * | 8/2003 | Miller et al. ............... 623/23.7 |

FOREIGN PATENT DOCUMENTS

| | | | |
|---|---|---|---|
| EP | 0 656 196 A1 | 6/1995 | |
| JP | 05-176947 | 7/1993 | |
| JP | 06-343688 | 12/1994 | |
| WO | WO 93/05730 | 4/1993 | |
| WO | WO 95/10247 | 4/1995 | |
| WO | WO 01/21107 A1 | 3/2001 | |
| WO | WO 01/32382 A1 * | 5/2001 | ........... B29B/15/10 |
| WO | WO 01/52914 A1 * | 7/2001 | ........... A61L/27/16 |
| WO | WO 01/67991 A1 | 9/2001 | |
| WO | WO 02/060351 A1 | 8/2002 | |

OTHER PUBLICATIONS

International Search Report for PCT/US03/25930.

* cited by examiner

Primary Examiner—Paul B. Prebilic
(74) Attorney, Agent, or Firm—Hoffman & Baron, LLP

(57) ABSTRACT

The present invention provides an implantable graft, including a primary tubular body having a first outer wall surface and a first inner wall surface defining a primary blood contacting lumen, and a secondary tubular body having a second outer wall surface and a second inner wall surface. The secondary tubular body is located about the primary tubular body to form a space therebetween. The primary and secondary tubular bodies are joined by at least one rib.

33 Claims, 7 Drawing Sheets

MULTI-LUMEN VASCULAR GRAFTS HAVING IMPROVED SELF-SEALING PROPERTIES

FIELD OF THE INVENTION

The present invention relates generally to an implantable prosthesis. More particularly, the present invention relates to an implantable graft having an integral multi-lumen structure.

BACKGROUND OF THE INVENTION

Implantable grafts are commonly used in treatment of diseased blood vessels. One such device is a synthetic vascular graft designed to replace damaged or dysfunctional tissue. Such damage or dysfunction can arise, for example, from arterial or venous pathways that have been damaged by thrombosis, an aneurysm or occlusion. The graft provides an artificial lumen through which blood may flow.

Natural blood vessels are often damaged during treatment of renal failure. For example, when treating patients with renal failure using dialysis, it is necessary to have ready access to blood vessels in order to continuously withdraw blood from the patient in amounts of over 200 ml/min. For dialysis to be effective, it must be repeated on a regular schedule of two or more treatments per week. Each time, a vein is accessed using a relatively large bore needle. As a result of the repeated percutaneous access, the vein will often collapse along the puncture tract or become aneurismal, leaky, or filled with clot. The latter can cause significant risk of pulmonary embolism. As a result, in dialysis treatments, artificial grafts have been used as an alternative to using a patient's own veins, in an attempt to avoid these complications.

Thus, one increasingly useful application of a vascular prosthesis is as a bypass shunt between an artery and a vein. A graft surgically placed between an artery and a vein (AV fistula) is commonly used in dialysis patients. This bypass or fistula is particularly useful for allowing multiple needle access, as is required for hemodialysis treatments.

Grafts can be made from a variety of materials such as textiles and formed polymers. Vascular grafts are often made from polytetrafluoroethylene (PTFE) tubes, and in particular, from expanded polytetrafluoroethylene (ePTFE) tubes. When PTFE is expanded or stretched to form tubes, the material consists of a unique microstructure of nodes interconnected by small fibrils. The space between the nodes that is spanned by the fibrils is defined as the internodal distance (IND). By varying the conditions of manufacture of the ePTFE tubes, such as temperature and rate of stretching and expansion, it is possible to vary the space between the nodes and the number and diameter of fibrils. Expanded PTFE is particularly suitable as an implantable prosthesis as it exhibits the desirable characteristics of superior biocompatibility and low thrombogenicity.

Expanded PTFE products that are stretched and expanded at high temperatures and rates are more homogeneous in structure. The IND is smaller and there are a greater number of fibrils in the ePTFE tubes. As a result, the product is stronger than if it had been made at lower temperatures and/or slower rates. In addition, the porosity is reduced. By varying the conditions of manufacture, it is possible to often obtain a final product having desired porosity, strength, and flex qualities.

It is a goal in graft technology to mimic, as closely as possible, the natural function of the blood vessel being replaced. This involves finding a graft material and design that will be sufficiently strong to resist tear and other mechanical damage, to be sufficiently flexible and compliant to accommodate the natural variability of flow and pressure of blood, and to be sufficiently porous to allow for enhanced healing and appropriate tissue ingrowth to anchor the prosthesis within the blood vessel and integrate it within the body.

The internal structure of ePTFE is desirable in a number of respects. The diameter of the fibrils formed in ePTFE is much smaller than the diameter of fibers of knitted or woven fabrics that have been used previously in vascular prostheses. Expanded PTFE tubes having a relatively large IND also possesses a higher degree of porosity than PTFE. These characteristics create a better substrate for cellular ingrowth, improved flexibility, and greater compliance in a graft. As a result, a prosthesis formed of ePTFE can more closely approximate the natural function of the blood vessel being replaced. Consequently, reduced thrombogenicity, reduced incidence of intima hyperplasia, and improved cellular ingrowth can be expected from ePTFE grafts as compared to a prosthesis formed of other presently available materials or unexpanded PTFE.

Current graft materials and designs have not fully achieved the desired result of mimicking natural vessels, and disadvantages of using the presently available ePTFE grafts remain. For example, when the IND is large so as to increase porosity and improved ingrowth, then the radial tensile strength of the tube is reduced as is the ability of the tube to retain sutures used during implantation. Such microporous tubes tend to exhibit low axial tear strength, so that a small tear or nick will tend to propagate along the length of the tube. Thus, there is a trade-off between optimal porosity and flexibility, and optimal strength.

In addition to the usual structural limitations of using ePTFE for grafts, there is an additional disadvantage of using implantable ePTFE vascular grafts as access shunts for hemodialysis. Specifically, it is difficult to elicit natural occlusion of suture holes created during implantation. As a result, the PTFE grafts are generally not used to withdraw blood until they have been in place for a minimum of 14 days after surgery. This time is required to allow time for protective ingrowth tissue to form and keep blood from leaking from the suture holes. Use of the graft before this period may result in complications such as a hematoma surrounding the graft, false aneurysm, and possibly graft occlusion. Thus, in order to maintain the integrity of the graft, blood cannot be withdrawn from a PTFE vascular graft until the suture holes have healed. However, waiting this amount of time to treat a dialysis patient causes undesirable build-up of toxins in the blood with its attendant problems.

A further problem associated with grafts used for hemodialysis is that repeatedly piercing the graft can compromise its integrity, causing large-scale tears in some instances, or more often result in hematomas where small amounts of blood leak from the needle entry point. A number of designs for ePTFE vascular grafts have been developed to address these problems.

For example, U.S. Pat. No. 4,619,641 discloses a two-piece coaxial double lumen arteriovenous graft. This graft consists of an outer tube positioned over an inner tube, the space between being filled with a self-sealing adhesive. The self-sealing adhesive helps prevent hematomas caused by piercing the graft. A disadvantage of this design is that completely filling the space between tubes with adhesive limits its flexibility and compliance.

In an attempt to increase radial tensile and axial tear strength of ePTFE tubes, U.S. Pat. No. 4,743,480 discloses a method of altering the extrusion process so as to reorient the fibrils in the node and fibril matrix.

U.S. Pat. No. 6,053,939 discloses a single layer ePTFE graft which releases heparin after grafting. Spaces between the nodes and fibrils are chemically treated to make the inner surface of the tube hydrophilic. Tissue-inducing substances and anti-thrombotic substances (such as heparin) are then covalently bonded to the hydrophilic inner surface of the tube and pores. The result is a high patency ratio and reduced risk of thrombosis. Although increased patency is achieved using this technology, there is still a period of delay before the graft can safely be used for dialysis. In addition, there is still a risk of hematoma caused by repeated piercing of the graft during dialysis.

U.S. Pat. No. 5,192,310 discloses a vascular graft having a primary lumen and at least one secondary lumen which share a common side wall. The secondary lumen is filled with a self-sealing, non-biodegradable, biocompatible polymer. However, this graft is difficult to make using traditional extrusion methods. The graft is made by using unconventional methods, involving a combination extrusion and injection molding process. As a result, the manufacture of this graft is expected to result in a non-uniform and irregular pattern of nodes and fibrils. This irregular conformation becomes problematic during the sintering step during which time melt fractures and other inconsistencies in the microstructure will occur. Thus, this disclosed method of making the graft appears unreliable, costly and likely to produce a defective product.

Thus, there is a need for a graft which provides desirable porosity, resists tears at suture holes, and resists blood flow through puncture holes caused by repeated needle access.

SUMMARY OF THE INVENTION

One advantage of the present invention is that there is provided a vascular graft having sufficient porosity, flexibility and strength to use in procedures requiring repeated needle access and which includes a self-sealing capability.

Another advantage of the present invention is that the inventive vascular grafts can be used within a short period of time after implantation without adverse impact to the integrity of the graft.

A still further advantage of the present invention is that the inventive grafts are easily and reliably manufactured.

Another advantage of the present invention is that the inventive grafts provide superior assimilation capabilities and resealable properties.

It is a further advantage of the present invention that a self-sealing graft is provided which performs a drug delivery function.

Briefly stated, the present invention provides an implantable graft, including a primary tubular body having a first outer wall surface and a first inner wall surface defining a primary blood contacting lumen; and a secondary tubular body having a second outer wall surface and a second inner wall surface. The secondary tubular body is located about the primary tubular body to form a space therebetween. The primary and secondary tubular bodies are joined by at least one rib.

The present invention further provides an implantable graft, including a primary tubular body formed of ePTFE having a first outer wall surface and a first inner wall surface defining a primary blood contacting lumen, a secondary tubular body formed of ePTFE having a second outer wall surface and a second inner wall surface, with the secondary tubular body being located about the primary tubular body to form a space therebetween. The primary and secondary tubular bodies are joined by at least one rib, the rib defining a plurality of secondary lumens. A self-sealing polymeric material may be located in at least one of the secondary lumens.

The present invention also provides a method of forming a self-sealing ePTFE graft. The method includes the steps of: (1) pre-forming a PTFE structure from PTFE paste into a tubular shape having a primary lumen and at least one peripherally located non-blood contacting lumen, and (2) extruding the pre-formed PTFE structure through a die having spacing devices for holding open the non-blood contacting lumen to form a multi-lumen tube.

Additionally, an implantable graft is provided, including a first tubular blood contacting member having a first inner wall surface and a first outer wall surface and defining a blood contacting lumen, a second tubular non-blood contacting member having a second inner wall surface and a second outer wall surface. The non-blood contacting member is arranged at least partially non-concentrically about the blood contacting member so as to define at least one non-blood contacting lumen therebetween. At least a portion of the first outer wall and the second inner wall are in contact and contiguous along a length of the graft. The members are laminated along said portion.

Further, the present invention also provides a method of forming a graft including: (1) extruding a first tubular member from PTFE paste having a first outer wall surface and a first inner wall surface defining a primary blood contacting lumen; (2) extruding a second tubular member from PTFE paste having a second outer wall surface and a second inner wall surface; (3) arranging the second tubular member non-concentrically about the first tubular member along a length of the graft such that a portion of the first outer wall contacts a portion of the second inner wall; and (4) laminating the members to one another where the members are in contact.

The invention will be more fully appreciated by reference to the following detailed description in conjunction with the attached drawing in which like reference numbers refer to like elements throughout the several views.

DETAILED DESCRIPTION OF THE INVENTION

The prosthesis of the present invention includes an implantable self-sealing tubular structure having a plurality of secondary lumens between a primary and a secondary tubular structure. Desirably, the prosthesis is formed from extruded PTFE or other similar material which exhibits superior biocompatibility.

In the present invention, a primary tubular body is formed which defines a blood contacting lumen. A secondary tubular structure is formed about and integral with the first tubular structure at an outer wall of the primary tubular body. A portion of an inner wall of the secondary tubular body and a portion of an outer wall of the primary tubular body defines at least one secondary lumen between the tubular bodies. The secondary lumen may contain a non-biodegradable self-sealing elastomeric material. Optionally, a pharmacologically or physiologically active agent may be supplied in the graft for delivery to the patient.

In an advantageous aspect of the invention, the device is a vascular graft implanted into the patient's arterial or venous system so that blood flow is established through the primary lumen.

Figure 1:
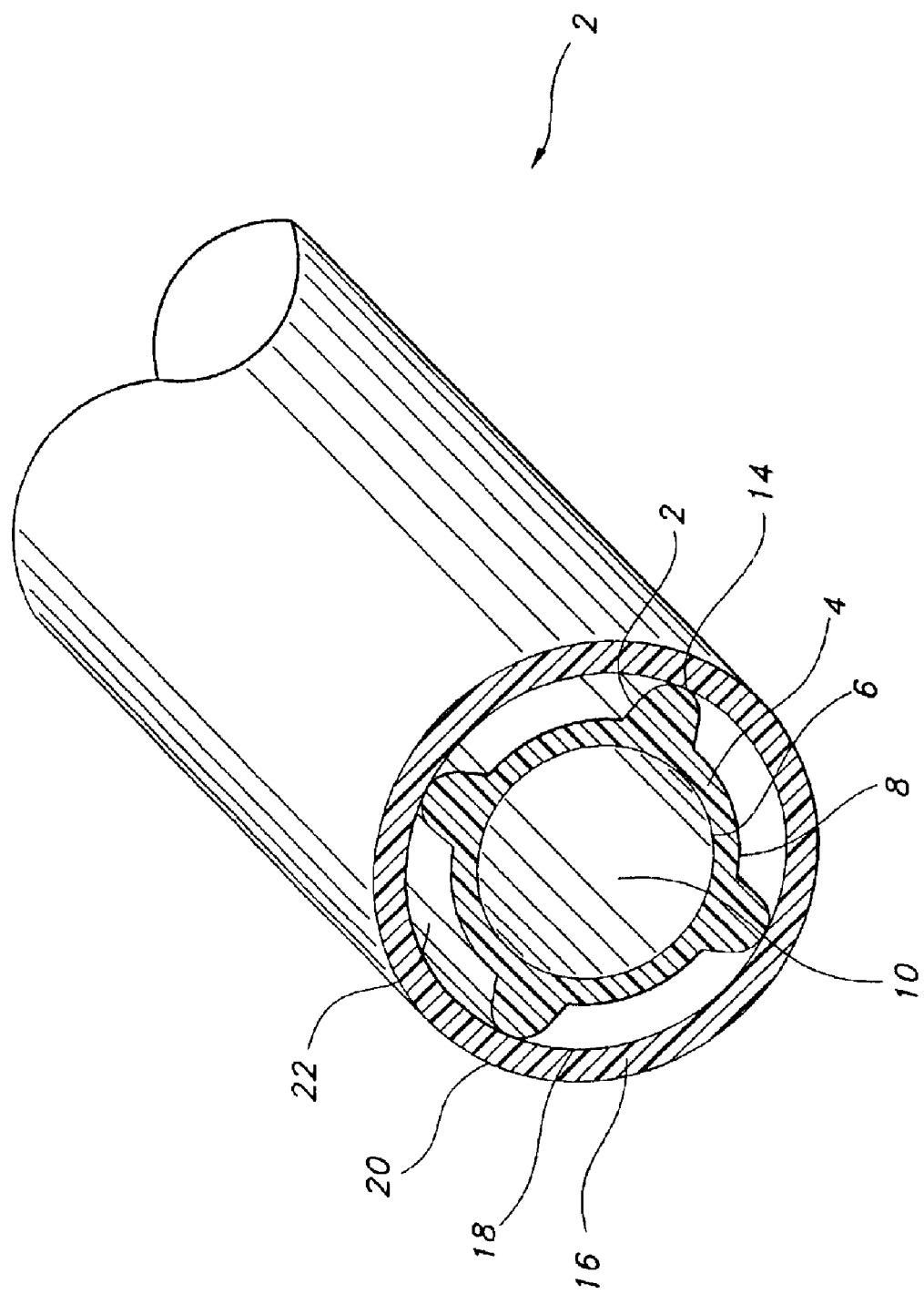
FIG. 1 is a perspective view of an implantable graft according to the present invention.

Referring now to FIG. 1, a multi-lumen graft of the present invention is shown. The graft, generally indicated by the numeral 2, is an elongate tubular structure including a primary tubular body 4 having an inner wall surface 6 and an outer wall surface 8. The inner wall surface 6 defines a blood contacting primary lumen 10. The primary tubular body 4 includes a plurality of ribs 12 each having a radial apex 14. A secondary tubular body 16 having an inner wall surface 18 and an outer wall surface 20 is arranged about the primary tubular body 4. The apexes 14 of the ribs 12 are in contact and integral with that portion of the inner wall surface 18 of the secondary tubular body 16 with which they are in contact. The outer wall 8 of the primary tubular body 4 and the inner wall 18 of the secondary tubular body 16 between the ribs 12 define a plurality of secondary lumens 22. These secondary lumens 22 are non-blood contacting. There is no particular limitation to the number of secondary lumens 22.

Although FIG. 1 shows four secondary lumens, there are no particular limitations to the number of secondary lumens present in the graft. Similarly, there is no particular limitation as to the shape of the secondary lumens, although a narrow cross-section is preferred so as to maintain a cross-sectional size of the graft which approximates, as closely as possible, the natural vessel being replaced. The ribs may be thin to separate the lumens or may be relatively thick to serve a structural support function as well. Relative thicknesses of the material forming the primary and secondary tubular bodies may be varied with respect to one another. In addition, the size and shape of the ribs and the secondary lumens may be the same or different.

Figure 2:
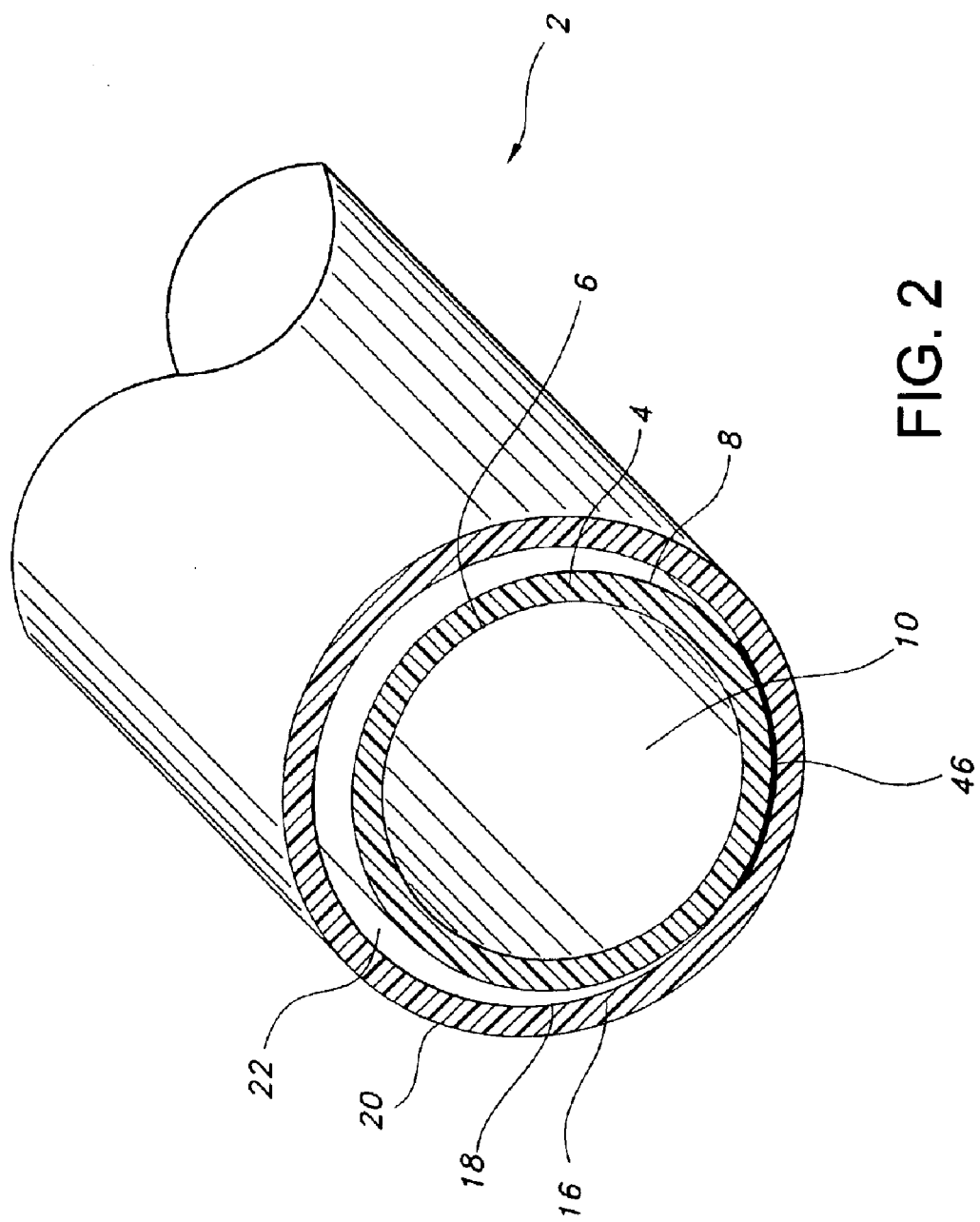
FIG. 2 is a perspective view of an alternative embodiment of the present invention.

Referring now to FIG. 2, an alternative embodiment of the multi-lumen graft according to the invention is shown. As in the previous embodiment, the graft 2 is comprised of a primary tubular body 4 having an inner wall surface 6 and an outer wall surface 8. The inner wall surface 6 defines a blood contacting primary lumen 10. A secondary tubular body 16 having an inner wall surface 18 and an outer wall surface 20 is arranged about the primary tubular body 4. In this embodiment, the primary tubular body 4 is arranged at least partially non-concentrically within the secondary tubular body 16 so that a portion of the outer wall surface 8 of the primary tubular body 4 and a portion of the inner wall surface 18 of the secondary tubular body 16 are in contact and are made integral by use of, for example, an adhesive 46. The portion of these walls that are not in contact define a secondary lumen 22. In this embodiment, there is a single secondary lumen 22 which is substantially crescent-shaped.

In a further aspect of the present invention, multiple layers of lumens including tertiary lumens are present on the graft. In this aspect, the graft may be designed so that access to the primary lumen is through at least one secondary lumen and one tertiary lumen.

Figure 3:
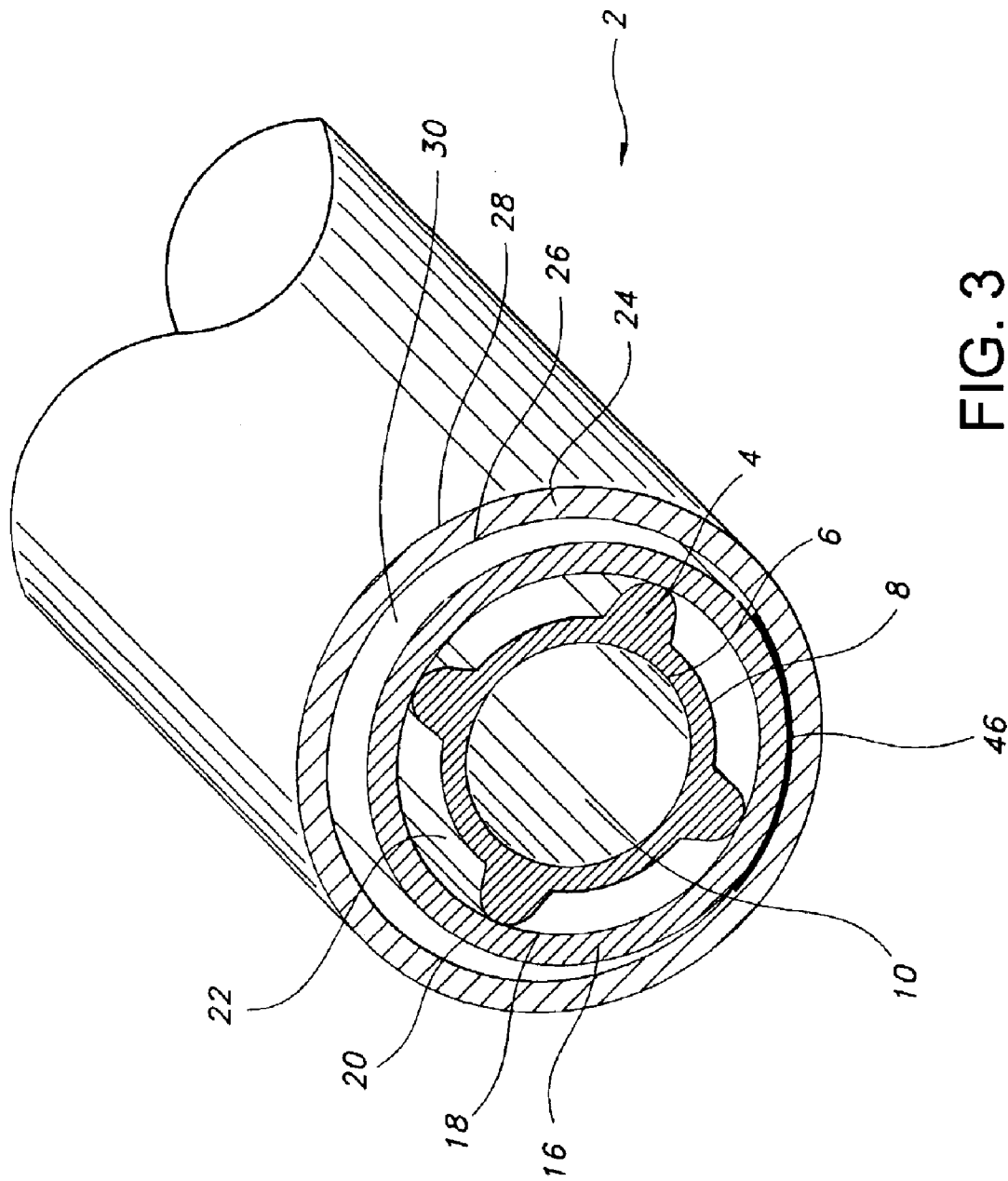
FIG. 3 is a perspective view of a further embodiment of the present invention including a tertiary lumen.

Referring now to FIG. 3, a further alternative embodiment of the multi-lumen graft according to the invention is shown. The structure of the graft is as described in the embodiment shown in FIG. 1. In this embodiment, there are four secondary lumens 22 arranged concentrically about the primary lumen 10. Additionally, a tertiary tubular body 24 is provided including an inner wall surface 26 and an outer wall surface 28. The tertiary tubular body 24 is arranged about the secondary tubular body 16 in a partially non-concentric manner so that a portion of the inner wall surface 26 of the tertiary tubular body 24 is in contact and made integral with a portion of the outer wall surface 20 of the secondary tubular body 16 by an adhesive 46. The portion of these walls that are not in contact define a tertiary lumen 30. In this embodiment, the secondary lumens 22 are arranged intermediate the primary lumen 10 and the tertiary lumen 30.

In this particular aspect of the invention, the tertiary lumen, which is closest to the skin or access point, includes a self-sealing material, while a secondary lumen, which is closer to the primary lumen through which blood flows, may include a self-sealing material and/or a physiologically or pharmacologically active agent.

Figure 7:
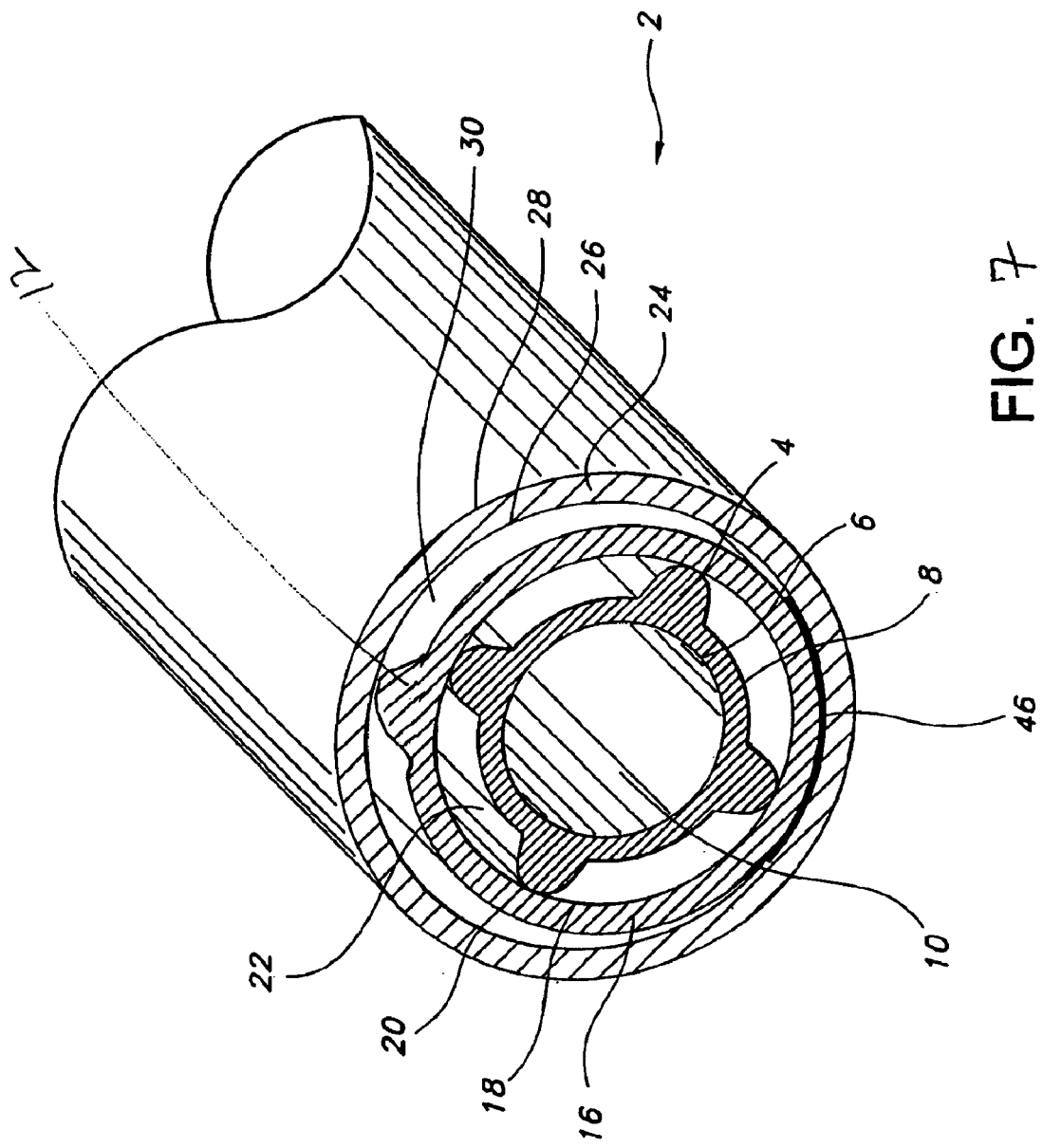
FIG. 7 is a perspective view of an embodiment of the present invention including a secondary tubular body that is joined to a tertiary tubular body by at least one secondary rib.

Referring to FIG. 7, a further alternative embodiment of the multi-lumen graft according to the invention is shown. The structure of the graft is as described in the embodiment shown in FIG. 3. In the embodiment shown in FIG. 7, the secondary tubular body 16 is attached to the tertiary tubular body 24 by at least one rib 12.

It is to be understood that the arrangement of contacting tubular bodies and tubular bodies connected by ribs may be used in any appropriate combination. Thus, the tubular bodies may be connected entirely by a ribbed connection, or entirely by non-concentric wall surface contact or any combination thereof.

In one advantageous aspect, the primary lumen is of a sufficient internal diameter (ID) to allow blood flow therethrough. This means that the ID of the primary lumen will typically be from about 3 mm to about 24 mm depending on the application.

The tubular structures of the present invention can be made from any suitable biocompatible material that can be arranged to form a microporous structure. Suitable materials include polyimides, silicone, polyurethanes, polyurethane ethers, polyurethane esters, polyurethane ureas, and mixtures and copolymers thereof. Desirable materials include polyethylene terephthalate (Dacron™ brand polyester), and other synthetic polyester fibers such as mandrel spun polyurethane and silicone elastomeric fibers. Particularly desirable polymeric materials which are useful for this purpose include fluoropolymers, for example, either expanded or unexpanded polytetrafluoroethylene (PTFE). At least one of the tubular bodies is desirably made from PTFE, more desirably at least the primary tubular body is formed from ePTFE.

In one advantageous aspect of the invention, the materials forming the lumens and ribs of the graft possess an internodal distance of from about 1 µm to 200 µm. Even more advantageously, the internodal distance is from about 10 µm to 100 µm.

In one advantageous aspect, the inventive graft is made using PTFE which possesses desirable porosity, radial tensile strength, and resistance to tears at suture points. Advantageously, at least the primary tubular body is formed of ePTFE having an internodal distance (IND) in excess of about 40 microns. Grafts having IND's in this range generally exhibit long-term patency as the larger pores promote formation of the intima layer along the inner blood contacting surface. Tubes having an IND less than about 40 microns exhibit lesser healing characteristics, however offer superior radial tensile strength and suture retention strength, and are also within the scope of the invention.

The inner and outer tubular bodies of the present invention may be formed by a variety of methods. For example, extrusion processes such as ram extrusion; polymeric casting techniques such as solvent casting and film casting; molding techniques such as blow molding, injection molding and rotational molding; and other thermoforming techniques useful with polymeric materials may be employed and chosen to best serve the type of material used and specific characteristics of the membrane desired.

One method for manufacturing porous PTFE tubing generally, is described, for example, in U.S. Pat. Nos. 3,953,566, 3,962,153, and 4,973,609, the entireties of which are herein incorporated by reference. Generally, a PTFE tube may be formed in four steps including preparation of a PTFE paste, extrusion of a tube, expansion of the tube, and sintering of the tube. Briefly, a PTFE paste dispersion is made for later extrusion by admixing a fine, virgin PTFE powder such as F-104, F-103, Virgin PTFE Fine Powder (Dakin America, Orangeburg, N.Y.) with a liquid lubricant such as odorless mineral spirits or naphtha, i.e., Isopar® (Exxon Chemical Co., Houston, Tex.), to form a PTFE paste of the desired consistency. The PTFE paste is either passed through a tubular extrusion dye or coated onto a mandrel to form a tubular extrudate. Next, the wet extrudate is dried to evaporate the lubricant at either room temperature or temperatures near the lubricant's dry point. After the PTFE resin or paste is formed and dried, it is stretched and/or expanded. Stretching refers to elongation of formed resin while expansion refers to enlargement of the formed resin perpendicularly to its longitudinal axis. The stretching/expansion step occurs at a temperature less than 327° C., typically in the range of 250–326° C. by an expansion rate of at least two to one (2:1). Finally, the tubular extrudate is sintered by heating it to a temperature of about 350–370° C. This results in an amorphous locking of the polymer.

The tubular bodies may be made integral at the rib apexes and wall surface contact points or the contacting wall surfaces in a variety of ways, depending on the particular materials which form the tubular bodies. Generally, as best shown in FIGS. 1–4, the primary and secondary tubular bodies 4 and 16 are laminated together at their points of contact. Numerous techniques may be employed to laminate or bond the primary tubular body 4 to the secondary tubular body 16. Heat setting, adhesive welding, application of uniform force and other bonding techniques known in the art may all be employed to bond or secure the tubular bodies 4 and 16 at their points of contact, be they rib 12 apexes 14 or contacting wall surfaces 8 and 18. In each of these bonding techniques, it is contemplated that the points of contact be made integral.

Alternatively, it is possible to form the tubular bodies integrally during an extrusion process. In this case, desirably, the mandrel, dye and mold for the graft are designed so as to evenly distribute and form the PTFE paste into a desired shape and to produce a graft having a uniform node and fibril structure throughout the graft.

Figure 6:
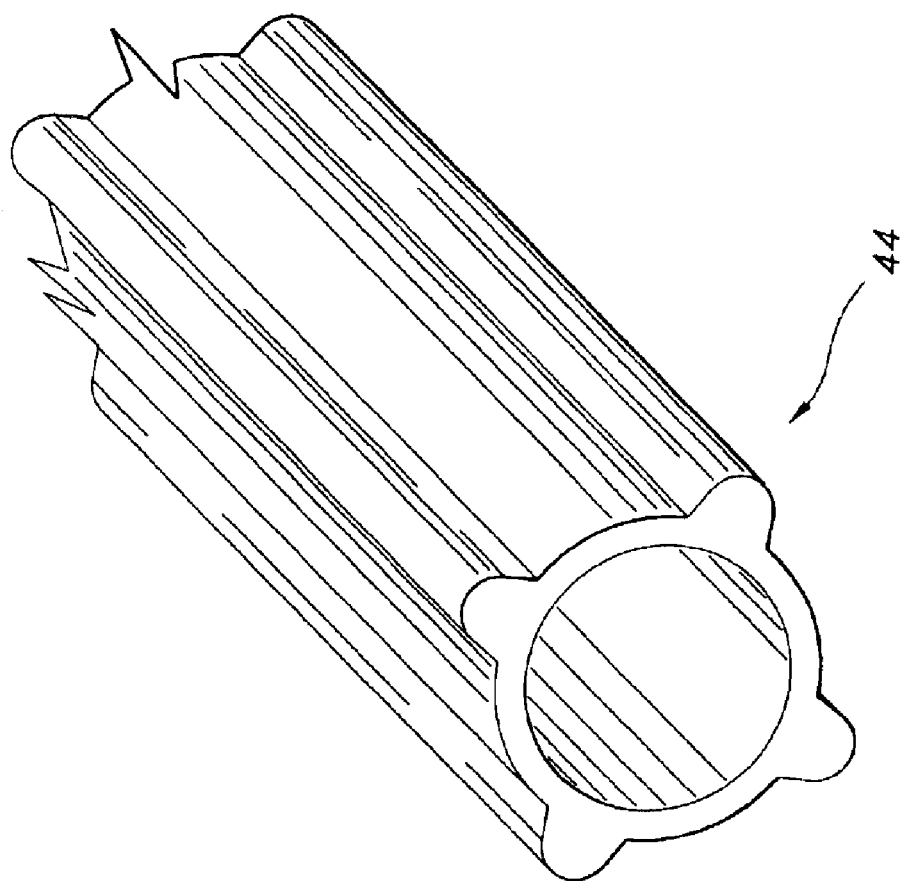
FIG. 6 is a perspective view of a die used to form the graft as shown in FIG. 1.

In one aspect of the invention, the tubular structures of the present invention which includes a rib or ribs may be formed of expanded PTFE by extrusion of a pre-formed PTFE structure having the shape of the final graft. Extrusion is performed using dies having the appropriate number of spacers to form the desired number of ribs. FIG. 6 is a perspective view of an exemplary die 44, corresponding to the illustrated graft of FIG. 1. The die 44 may be manufactured from materials available and well known in the art. A die mold in the form of a hollow cylinder (not shown) is placed around the die and the extrudate forms the graft by passing therethrough.

In grafts formed from ePTFE, the rate of stretching and the stretch ratio affect the porosity of the finished product in a predictable manner allowing a prosthetic device to be produced having a specified porosity. The rate of stretching refers to the percentage of elongation per second that the resin is stretched while the stretch ratio refers to the relationship between the final length of the stretched resin and the initial length of the stretched resin. For example, stretching an extruded PTFE tube at a stretch ratio of two to one and a stretch rate of sixty results in a porosity of approximately 40. This porosity is a unit-less number as determined in accord with the American Society For Testing of Materials' (ASTM's) Special Technical Publication Number 898. For example, based on stretch ratios ranging from two to one, to six to one, a stretch rate of sixty percent per second yields a porosity of between approximately 40 and approximately 90. A stretch rate of one hundred and forty percent per second at this ratio yields a porosity of between approximately 60 and approximately 85. Finally, a stretch rate of nine hundred percent per second at this same ratio yields a porosity of between approximately 65 and approximately 85.

In addition to the internodal distance and porosity, the geometry of the node and fibril network of PTFE can be controlled during stretching and expansion. In the case of uniaxial stretching, that is, elongation of the formed PTFE resin along the direction of extrusion, the nodes are elongated causing the longer axis of each node to be oriented perpendicularly to the direction of stretch. Accordingly, the fibrils are oriented parallel to the direction of stretch. Biaxial stretching additionally includes expanding the PTFE resin in the radial direction and can be utilized to produce a prosthetic device having a composite porosity. As in uniaxial stretching, the rate and ratio of radial expansion affects the resulting porosity of the prosthetic device.

In a particularly advantageous aspect of the invention, the geometry of the node and fibril network of ePTFE includes nodes oriented perpendicular to the direction of stretch. In a particularly preferred aspect, the nodes are uniformly oriented perpendicular to the direction of stretch.

In a further aspect of the present invention, one or more of the secondary lumens desirably include a non-biodegradable polymeric material which self-compresses after puncture by a needle so as to seal the puncture site. This material serves a self-sealing function in the graft of the present invention. Desirably, the self-sealing material is biocompatible.

A number of different materials may serve as the self-sealing polymeric material contemplated in the present invention. Some materials which may be used as a self sealing component in various forms include, but are not limited to, polymers and copolymers, including thermoplastic elastomers and certain silicones, silicone rubbers, synthetic rubbers, polyurethanes, polyethers, polyesters, polyamides and various fluoropolymers, including, but not limited to, PTFE, ePTFE, FEP (fluorinated ethylene propylene copolymer), and PFA (polyfluorinated alkanoate).

Furthermore, an exterior of the graft or a secondary lumen may be coated with an elastomeric material such as fluorine rubber, silicone rubber, urethane rubber, acrylic rubber or natural rubber to perform the self-sealing function. Among the fluorine rubber materials are a vinylidene fluoride/hexafluoropropylene copolymer, a vinylidine fluoride/chlorotrifluoroethylene copolymer, and a tetrafluoroethylene/propylene copolymer.

Preferably, the self-sealing polymeric material is crosslinked. For example, a fluorine rubber may be compounded with an acid acceptor, a crosslinking agent, and if desired, a filler before crosslinking. Examples of the acid acceptor are magnesium oxide and calcium oxide. Examples of the crosslinking agent are aliphatic polyamine derivatives, organic peroxides, and isocyanates. A typical compounding composition includes 100 parts by weight of a vinylidene fluoride/hexafluoropropylene copolymer, 15 parts of magnesium oxide, and 0.5 to 3 parts by weight of an aliphatic polyamine derivative. Preferably, the material is in a cross-linked state so as to prevent deterioration in the body.

The self-sealing material may be introduced into the graft by adhering in a layer to at least one surface of the primary and secondary tubular bodies. The adhesion may take place by mechanical means, chemical means (use of an adhesive), thermobonding or combinations thereof. Some polymers, particularly thermoplastic elastomers, become sufficiently tacky through heating to adhere to ePTFE tubular structures.

In use, the self-sealing component may function by exerting a force in the direction of the puncture. If the self-sealing material is adhered to both the primary and secondary tubular bodies, then either layer or both will seal the puncture site.

It is further within the purview of the present invention to include a flowable polymeric material as the self-sealing material. The term flowable as used herein refers to an amorphous material which fills a void created by a deformation or puncture.

A number of different flowable polymer layers may also be employed in the secondary and/or tertiary lumens to provide a self-sealing graft. The flowable polymer layer seals the graft by possessing an amorphous quality which fills in any space left open subsequent to puncture of the graft. It may simply fill in the space left open or it may additionally penetrate into the punctured secondary lumen to fill any void left from puncture of a tubular body.

An example of a flowable polymer which may be used as the self-sealing polymeric material in the present invention is an uncured or partially cured polymer. The polymer may be cured by a number of activating means which would activate curing subsequent to puncture of the graft, thereby sealing with the curing of the polymer. Examples of materials for such a flowable layer include, but are not limited to, uncured elastomers such as natural or synthetic rubbers, and natural gums such as gum arabic. Materials that are particularly useful in a flowable layer include non-crosslinked polyisobutylene which is also known as uncured butyl rubber.

Another flowable polymer layer which may be employed in the present invention is a gel. Gels are generally suspensions or emulsions of polymers which have properties intermediate between that of the liquid and solid states. A hydrogel may also be used in the present invention, and refers to polymeric material which swells in water without dissolving, and which retains a significant amount of water in its structure. The gels and hydrogels employed in the present invention may be biodegradable, or non-biodegradable. They also further may have polymeric beads suspended within the gel to effectuate sealing of the graft. Some examples of gels which may be used in the present invention include, but are not limited to, silicone gels, gum arabic, and low molecular weight ethylene/vinyl acetate polymers.

Suitable gels further include hydrogels formed from natural materials including, but not limited to, gelatin, collagen, albumin, casein, algin, carboxy methyl cellulose, carageenan, furcellaran, agarose, guar, locust bean gum, gum arabic, hydroxyethyl cellulose, hydroxypropyl cellulose, methyl cellulose, hydroxyalkylmethyl cellulose, pectin, partially deacetylated chitosan, starch and starch derivatives, including amylose and amylopectin, xanthan, polylysine, hyaluronic acid, and its derivatives, their salts, and mixtures thereof.

In an advantageous aspect, a physiologically or pharmacologically active agent may be coated or otherwise incorporated into the graft according to the invention. Any drug or bio-therapeutic agent may be coated onto a surface or incorporated into a lumen of the graft of the present invention. Examples of suitable drugs or bio-therapeutic agents may include, without limitation, thrombo-resistant agents, antibiotic agents, anti-tumor agents, cell cycle regulating agents, their homologs, derivatives, fragments, pharmaceutical salts, and combinations thereof.

Useful thrombo-resistant agents may include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics may include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof.

Useful anti-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Useful anti-viral agents may include, for example, amantadines, rimantadines, ribavirins, idoxuridines, vidarabines, trifluridines, acyclovirs, gancyclovirs, zidovudines, foscarnets, interferons, their homologs, analogs, fragments, derivatives, pharmaceutical salts and mixtures thereof The agent may be provided in any of a variety of methods. For example, it is possible to form the graft with monomers including functional groups to which the agents will bind. The graft can be dip coated with a mixture of a drug in an appropriate buffer. After allowing the drug to react with the functional groups, the graft may be dried. See the method as taught in U.S. Pat. No. 6,358,557, for example. Alternatively, it is also possible to use the porous nature of the graft material to hold therapeutic agents therein. The therapeutic agent may be added to the graft by addition of a therapeutic drug solution under pressure. Furthermore, it may be possible to add a therapeutic agent containing gel to one or more secondary lumens and to perforate portions of the wall surfaces of the tubular bodies to create pores for dispensing the gel slowly into the primary lumen or an exterior of the graft over time.

Figure 4:
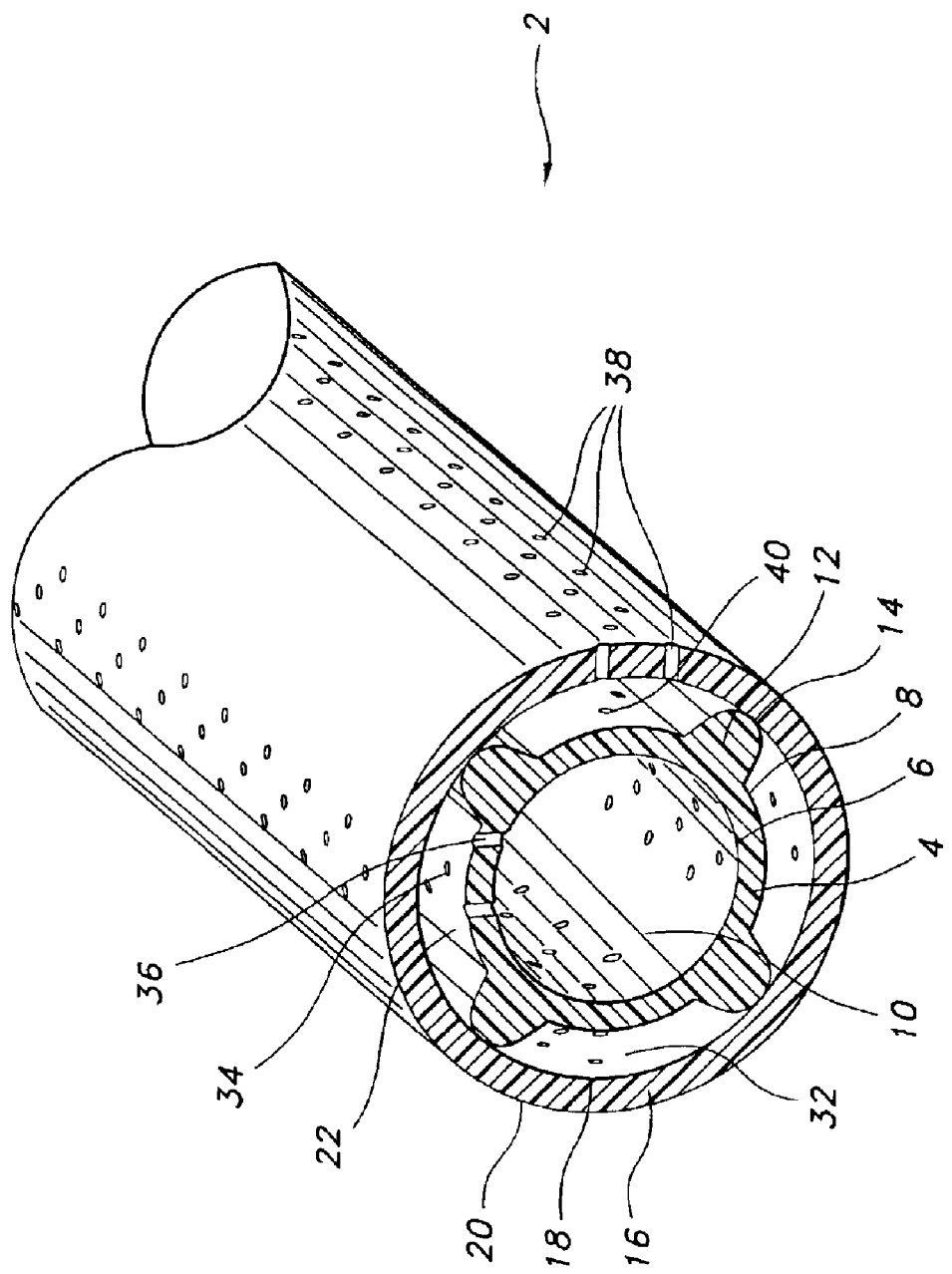
FIG. 4 is a perspective view of a further embodiment of the present invention including: a self-sealing elastomeric material, a plurality of drugs, and drug delivery pores in secondary lumens according to the present invention.

Referring now to FIG. 4, a multi-lumen graft 2 according to the invention includes a self-sealing polymeric material 32 in one of the secondary lumens 22. Another of the secondary lumens 22 includes a first drug 34 for treating a patient intravenously. The graft further includes secondary pores 38 arranged between a secondary lumen 22 and the secondary tubular body 16. A further drug 40 may be provided to a patient via the secondary pores 38. It is to be understood that, although the self-sealing polymeric material and the drugs are in separate lumens, it is also possible for a single lumen to contain one or more drugs as well as the self-sealing polymeric material. For example, it is possible to coat a surface of a secondary lumen adjacent the primary lumen surface with a material containing dissolvable time-released drug in a lumen filled with a self-sealing gel. The timed-release drug may enter the bloodstream while the self-sealing gel performs its function. The timed release of the drug does not necessarily rely on structural pores for drug delivery. It is possible for the drug to penetrate the intact surface of the secondary lumen.

Figure 5:
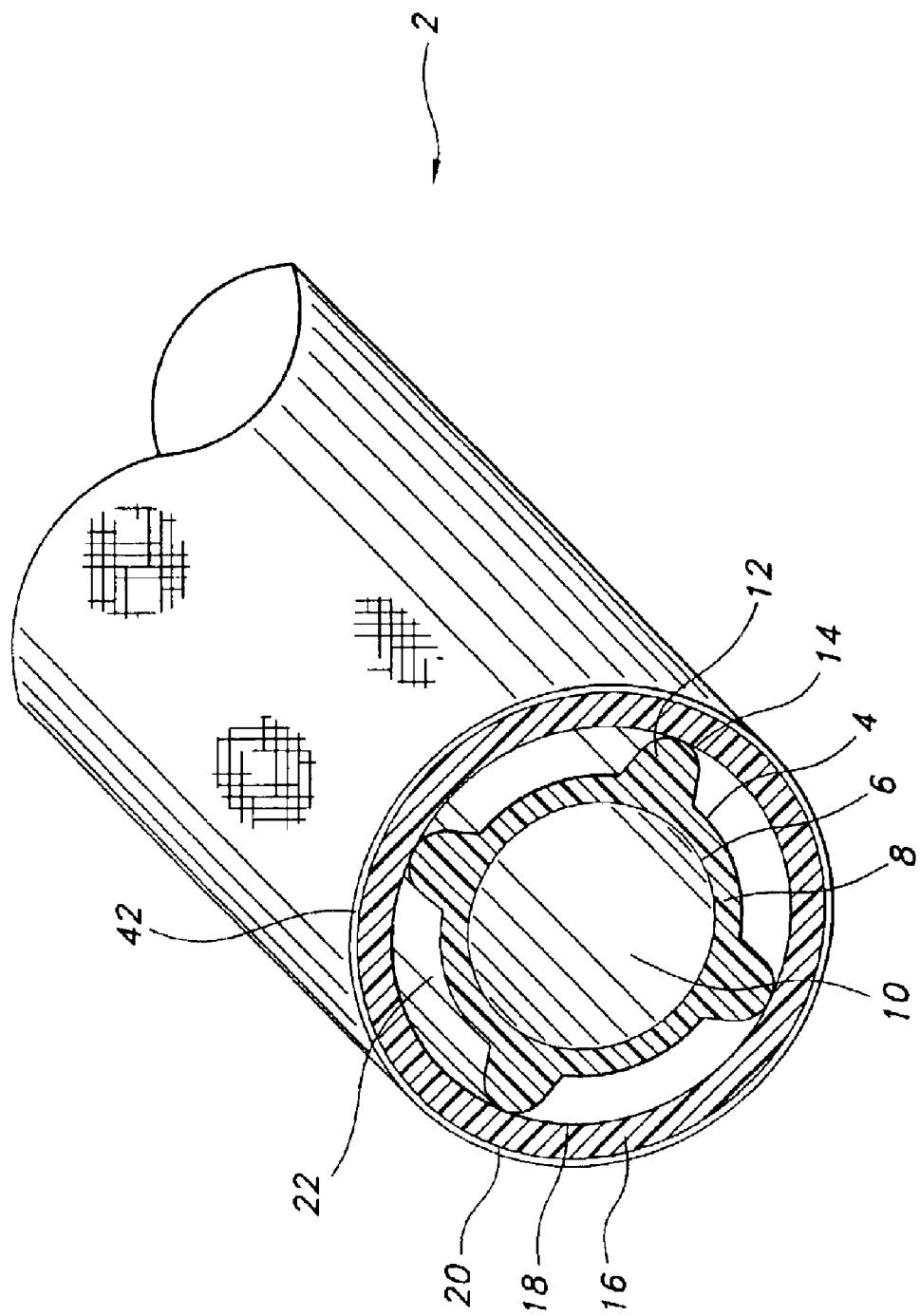
FIG. 5 is a perspective view of an embodiment of the present invention including a textile material around an exterior of the graft according to the present invention.

In a further aspect of the invention, the graft may further include a support member such as a textile layer or sleeve on one or more of an exterior or an interior of the graft. A suitable textile for this purpose is a knit biocompatible material such as polyester or polyethylene terephthalate (DACRON), for example. Referring now to FIG. 5, a textile sleeve 42 is shown covering the multi-lumen graft 2. The textile sleeve 42 serves to provide additional strength to the implant, and/or to aid in resisting tear from suture holes.

The graft according to the present invention may be used advantageously, for example, in implanting a self-sealing graft device to replace or augment part of an arteriovenous (AV) pathway in an individual in need thereof In the method, a surgeon or other qualified person surgically exposes the desired region for introduction of the graft of the invention. The desired site may be an area of occlusion or weakness in the patient's arteriovascular system, or the site for an AV bypass in a dialysis patient, for example. An interruption of the patient's blood flow is performed, and the device is surgically implanted and sutured or otherwise secured in place so that blood flow is established through the primary lumen. Once the graft is in place, the bloodstream can be accessed by a cannula, intravenous needle or the like through a secondary lumen. When the cannula or needle is withdrawn, the self-sealing elastomeric material on the secondary lumen will block access of blood to the puncture hole created by the needle, thus preventing blood from escaping from the area of access.

The grafts of the present invention are particularly suited for use as AV bypasses for dialysis patients. The graft will be resistant to leaks at suture holes because many of the suture holes will be formed through the secondary lumens containing the self-sealing material. This will allow use of the implant without having to wait extended periods of time to heal suture hole leaks. Further, even after repeated access to the device by a large bore needle, the implant will resist leakage of blood from the primary lumen. Additionally, if a drug delivery aspect is included in the graft, appropriate therapeutic drugs will be available at the site of injury to facilitate fast and reliable healing.

The invention may be embodied in other specific forms without departing from the spirit of essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An implantable graft, comprising:

a primary tubular body having an outer wall surface and an inner wall surface defining a primary blood-contacting lumen; and a secondary tubular body having an outer wall surface and an inner wall surface, said secondary tubular body being located about said primary tubular body, wherein said primary and secondary tubular bodies are joined by at least two ribs, wherein the outer wall surface of the primary tubular body, the inner wall surface of the secondary tubular body, and the at least two ribs define a plurality of secondary lumens, wherein a self-sealing polymeric material is present in at least one of said plurality of secondary lumens, and wherein a drug is present in at least one of said plurality of secondary lumens.

2. The graft according to claim 1, wherein at least one of said tubular bodies is made of a fluoropolymer, a polyimide, a silicone, a polyurethane, a polyurethane ether, a polyurethane ester, a polyurethaneurea, and mixtures and copolymers thereof.

3. The graft according to claim 1, wherein at least one of said tubular bodies is made from expanded PTFE.

4. The graft according to claim 3, wherein said graft includes substantially uniformly spaced and oriented node and fibril ePTFE structures throughout said graft.

5. The graft according to claim 1, wherein said self-sealing polymeric material is selected from the group consisting of elastomeric polymers and elastomeric copolymers.

6. The graft according to claim 1, wherein said self-sealing polymeric material is selected from the group consisting of a silicone rubber, a polyurethane, and a polyether.

7. The graft according to claim 6, wherein said self-sealing polymeric material further comprises a flowable layer.

8. The graft according to claim 7, wherein said self-sealing polymeric material further comprises a gel.

9. The graft according to claim 8, wherein said gel is selected from the group consisting of a silicone gel, a gum arabic, a low molecular weight ethylene/vinyl acetate polymer, and an uncured rubber.

10. The graft according to claim 8, wherein said flowable layer includes an uncured polymer.

11. The graft according to claim 8, wherein said flowable layer a polymer that is at least partially cured.

12. The graft according to claim 8, wherein said gel is non-crosslinked polyisobutylene.

13. The graft according to claim 1, comprising from about 2 to 5 ribs.

14. The graft according to claim 1, further comprising at least one drug present on the surface of said primary lumen.

15. The graft according to claim 1, wherein said drug is present in a carrier.

16. The graft according to claim 15, further comprising drug delivery means for delivering said drug to said primary lumen.

17. The graft according to claim 16, wherein said drug delivery means comprises a plurality of pores in a portion of said primary tubular body which defines said remainder of said plurality of secondary lumens in which said drug is present.

18. The graft according to claim 17, wherein said drug is selected from the group consisting of an anticoagulant, an antibiotic, an anti-thrombogenic, an anti-inflammatory agent, an anesthetic agent, an anti-coagulant, a vascular cell growth promoter, a vascular cell growth inhibitor, and a cholesterol-lowering agent.

19. The graft according to claim 15, further comprising drug delivery means for delivering said drug to an exterior space outside of said graft.

20. The graft according to claim 19, wherein said drug delivery means comprises a plurality of pores in a portion of said secondary tubular body which defines said remainder of said plurality of secondary lumens.

21. The graft according to claim 20, wherein said drug is selected from the group consisting of an anticoagulant, an antibiotic agent, an anti-thrombogenic agent, an anti-inflammatory agent, an anesthetic agent, an anti-coagulant, a vascular cell growth promoter, a vascular cell growth inhibitor, and a cholesterol-lowering agent.

22. The graft according to claim 1, further comprising a support material arranged on at least one of the inner wall surface of the primary tubular body and the outer wall surface of the secondary tubular body.

23. The graft according to claim 22, wherein said support material is selected from the group consisting of an elastomeric material and a textile.

24. The graft according to claim 23, wherein said support material is a textile and further comprising a bonding agent for bonding said textile to said graft.

25. The graft according to claim 24, wherein said textile is polyethylene terephthalate.

26. The graft according to claim 1, further comprising a tertiary tubular body having a third inner wall surface and a third outer wall surface, said tertiary tubular body being located about said secondary tubular body to form a space therebetween, wherein said secondary and tertiary bodies are joined by at least one secondary rib.

27. An implantable graft, comprising:
a primary tubular body having an outer wall surface and an inner wall surface defining a primary blood-contacting lumen; and a secondary tubular body having an outer wall surface and an inner wall surface, said secondary tubular body being located about said primary tubular body to form a space therebetween; wherein said primary and secondary tubular bodies are joined by at least one rib; wherein a self-sealing polymeric material selected from the group consisting of a silicone rubber, a polyurethane, and a polyether is located in said space; and wherein the self-sealing polymeric material further comprises a flowable layer and a non-crosslinked polyisobutylene.

28. An implantable graft, comprising:
a primary tubular body having a first outer wall surface and a first inner wall surface defining a primary blood-contacting lumen; and
a secondary tubular body having a second outer wall surface and a second inner wall surface, said secondary tubular body being located about said primary tubular body to form a space therebetween, wherein said primary and secondary tubular bodies are joined by at least one rib, wherein the graft comprises a self-sealing polymeric material selected from the group consisting of a silicone rubber, a polyurethane, and a polyether, wherein the self-sealing polymeric material further comprises a flowable layer and non-crosslinked polyisobutylene.

29. An implantable graft, comprising:
a primary tubular body having a first outer wall surface and a first inner wall surface defining a primary blood-contacting lumen; and
a secondary tubular body having a second outer wall surface and a second inner wall surface, said secondary tubular body being located about said primary tubular body to form a space therebetween, wherein said graft further comprises from about 2 to 5 ribs which define a plurality of secondary lumens, wherein a self-sealing polymeric material is located in at least one of said secondary lumens, wherein at least one drug in a carrier is present in or on a surface of at least one of said primary lumen and said plurality of secondary lumens, wherein said drug is present in at least one of said plurality of secondary lumens and said drug is present in at least one of a remainder of said plurality of secondary lumens in which said resealable polymer is not present.

30. The graft according to claim 29, further comprising drug delivery means for delivering said drug to an exterior space outside of said graft.

31. The graft according to claim 30, said drug delivery means comprises a plurality of pores in a portion of said secondary tubular body which defines said remainder of said plurality of secondary lumens.

32. The graft according to claim 31, wherein said drug is selected from the group consisting of an anticoagulant, an antibiotic agent, an anti-thrombogenic agent, an anti-inflammatory agent, an anesthetic agent, an anti-coagulant, a vascular cell growth promoter, a vascular cell growth inhibitor, and a cholesterol-lowering agent.

33. An implantable graft, comprising: a primary tubular body having an outer wall surface and an inner wall surface defining a primary blood-contacting lumen; and a secondary tubular body having an outer wall surface and an inner wall surface, said secondary tubular body being located about said primary tubular body to form a space therebetween, wherein said primary and secondary tubular bodies are joined by at least one rib, and wherein said graft further comprises a tertiary tubular body having an inner wall surface and an outer wall surface, said tertiary tubular body being located about said secondary tubular body to form a space therebetween, wherein said secondary and tertiary bodies are joined by at least one rib.

* * * * *

UNITED STATES PATENT AND TRADEMARK OFFICE
CERTIFICATE OF CORRECTION

PATENT NO. : 6,926,735 B2  Page 1 of 1
APPLICATION NO. : 10/328081
DATED : August 9, 2005
INVENTOR(S) : J. Henderson It is certified that error appears in the above-identified patent and that said Letters Patent is hereby corrected as shown below:

Item (74) on the Title page, the printed patent should read --Hoffmann & Baron, LLP--.

Column, 12, claim 11, lines 62-63, the printed patent should read --...said flowable layer includes a polymer that...--.

Signed and Sealed this

Fifth Day of December, 2006

JON W. DUDAS
*Director of the United States Patent and Trademark Office*